(12) United States Patent
Hui et al.

(10) Patent No.: US 10,548,606 B2
(45) Date of Patent: Feb. 4, 2020

(54) OCCLUSIVE COIL

(71) Applicant: Penumbra, Inc., Alameda, CA (US)

(72) Inventors: Delilah Hui, American Canyon, CA (US); Ben Tompkins, Danville, CA (US)

(73) Assignee: Penumbra, Inc., Alameda, CA (US)

( * ) Notice: Subject to any disclaimer, the term of this patent is extended or adjusted under 35 U.S.C. 154(b) by 1253 days.

(21) Appl. No.: 14/154,395

(22) Filed: Jan. 14, 2014

(65) Prior Publication Data

US 2014/0128907 A1 May 8, 2014

(51) Int. Cl.
*A61B 17/12* (2006.01)
*B29C 53/32* (2006.01)
*B29C 65/00* (2006.01)

(52) U.S. Cl.
CPC .. *A61B 17/12145* (2013.01); *A61B 17/12109* (2013.01); *B29C 53/32* (2013.01); *B29C 65/00* (2013.01); *Y10T 156/1002* (2015.01)

(58) Field of Classification Search
CPC ........ A61B 17/12113; A61B 17/12154; A61B 17/1214–12154; A61B 17/12109–12122; A61F 6/20; A61F 6/22
See application file for complete search history.

(56) References Cited

U.S. PATENT DOCUMENTS 5,122,136 A * 6/1992 Guglielmi ........ A61B 17/12022
606/585
5,154,705 A * 10/1992 Fleischhacker .... A61B 17/3207
600/585
5,853,418 A * 12/1998 Ken ................. A61B 17/12022
606/191
6,280,457 B1 * 8/2001 Wallace ........... A61B 17/12022
606/191
7,166,122 B2 * 1/2007 Aganon ........... A61B 17/12022
606/200
2004/0034378 A1 2/2004 Monstadt et al.
(Continued)

FOREIGN PATENT DOCUMENTS

CN 1298287 A 6/2001
CN 103356258 A 10/2013
(Continued)

OTHER PUBLICATIONS

Arko, et al. Endovascular repair reduces early and late morbidity compared to open surgery for abdominal aortic aneurysm. J Endovasc Ther. Dec. 2002;9(6):711-8.
(Continued)

*Primary Examiner* — Katherine M Shi
*Assistant Examiner* — Lindsey Bachman
(74) *Attorney, Agent, or Firm* — Wilson Sonsini Goodrich & Rosati

(57) ABSTRACT

Vessel occlusion coils disclosed that have a primary configuration for delivery and a secondary configuration for deployment that is conferred upon the devices by a stretch resistant member. In the secondary configuration, the stretch resistant member forms a stiffer coil and may have a greater diameter, and a more complex shape having some interior space, at one end than at the other end, for improved anchoring of the device in the vessel. The methods include intravascular delivery and deployment for implanting one or more vessel occlusion devices.

9 Claims, 5 Drawing Sheets

(56) References Cited

U.S. PATENT DOCUMENTS

| | | |
|---|---|---|
| 2006/0100661 A1 | 5/2006 | Jaeger et al. |
| 2008/0103585 A1* | 5/2008 | Monstadt ......... A61B 17/12022 623/1.22 |
| 2008/0306503 A1* | 12/2008 | Que ................. A61B 17/12022 606/191 |
| 2009/0062812 A1 | 3/2009 | Fitz et al. |
| 2010/0076479 A1 | 3/2010 | Monstadt |
| 2010/0137898 A1 | 6/2010 | Teoh |
| 2010/0174301 A1 | 7/2010 | Wallace et al. |
| 2010/0268204 A1 | 10/2010 | Tieu et al. |
| 2011/0184454 A1* | 7/2011 | Barry ............... A61B 17/12022 606/200 |
| 2012/0078285 A1 | 3/2012 | Griffin |
| 2012/0089174 A1 | 4/2012 | Chen et al. |
| 2012/0209310 A1 | 8/2012 | Chen et al. |
| 2013/0261659 A1 | 10/2013 | Lorenzo |
| 2013/0331882 A1 | 12/2013 | Tompkins et al. |
| 2014/0277100 A1 | 9/2014 | Kang |

FOREIGN PATENT DOCUMENTS

| | | |
|---|---|---|
| EP | 1889577 A1 | 2/2008 |
| EP | 2505150 A1 | 10/2012 |
| EP | 2644129 A2 | 10/2013 |
| EP | 2674114 A1 | 12/2013 |
| JP | 2003501131 A | 1/2003 |
| JP | 2005533615 A | 11/2005 |
| WO | WO-2008112435 A2 | 9/2008 |
| WO | WO 2010/096541 A1 | 8/2010 |

OTHER PUBLICATIONS

International search report and written opinion dated May 5, 2015 for PCT/US2015/011449.
U.S. Appl. No. 14/562,532, filed Dec. 5, 2014, Rabkin et al.
European Search Report dated Jun. 20, 2017 for EP Application No. 15737622.9.
Office action dated Feb. 23, 2018 for U.S. Appl. No. 14/562,532.
"Office action dated Aug. 9, 2018 for U.S. Appl. No. 14/562,532".
"Office action dated Sep. 21, 2018 for U.S. Appl. No. 14/154,395.".
Office action dated Jun. 12, 2019 for U.S. Appl. No. 14/562,532.

* cited by examiner

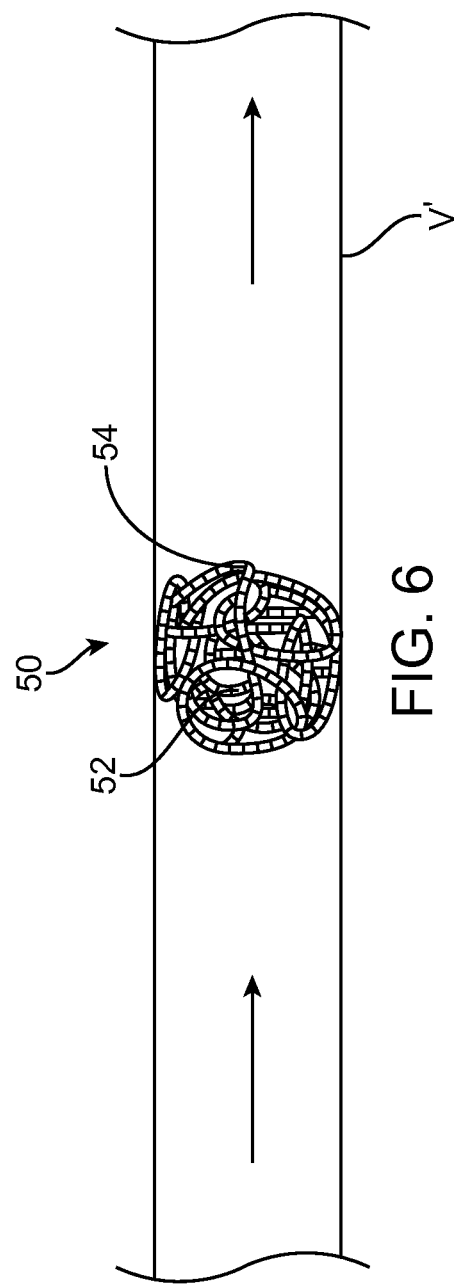

OCCLUSIVE COIL

FIELD OF THE INVENTION

The present invention relates generally to medical devices and medical treatment. Specifically, the invention relates to intravascular systems and methods for therapeutic vessel occlusion and aneurysm occlusion. Vessel occlusion may be desired for the treatment of vascular disease, treatment of tumors, and in the treatment of other disorders.

BACKGROUND OF THE INVENTION

Vessel occlusion may be a desirable therapeutic option in the treatment of various diseases of the body. Occlusion of otherwise healthy vessels, sometimes referred to as vessel sacrifice, may be undertaken in conjunction with other therapies, usually to augment these other therapies. For example, in the case of a cancerous tumor, it may be desirable to occlude or sacrifice a tumor feeder vessel in order to disrupt or prevent blood flow to the tumor, with the objective of shrinking the tumor or eliminating it entirely. Though the vessel providing blood flow to the tumor is healthy, it may be worthwhile to sacrifice it in order to prevent growth of the tumor or shrink the tumor. Such a procedure may be undertaken either alone, prior to surgical removal of the tumor, or in conjunction with radiation therapy. As another example, it may be desirable to occlude the internal iliac artery in a patient undergoing aortic or iliac aneurysm repair. The objective of the procedure would be to reduce blood flow into the vessel with the aneurysm, and it would be performed in addition to occlusion of the aneurysm. Another example of desirable vessel sacrifice is the occlusion of the gastroduodenal artery prior to selective internal radiotherapy, to prevent digestive ulcers caused by migration of radioactive particles. In addition to the foregoing examples, there are numerous other therapies in which it may be desirable to sacrifice a blood vessel.

Many devices and methods for the occlusion of or sacrifice of vessels are known in the art. The devices and methods are useful in the cerebral, coronary, and peripheral vasculature. Many known procedures require highly invasive surgery and thus carry many risks. In contrast, endovascular repair compared to open surgery has been reported to reduce early and late morbidity by half. Complications that require invasive or secondary surgical procedures and hospitalization are also reduced with endovascular repair. *J Endovasc Ther.* 2002 December; 9(6):711-8. Consequently, many of the developments in the art utilize intravascular techniques and devices.

Included among intravascular occlusion devices and methods known in the art are embolic particles, such as coils, that are delivered via intravascular catheter techniques. Embolic particles and coils may be fabricated from metals such as Nitinol, platinum or stainless steel, or polymers, including polymers exhibiting shape memory characteristics. A typical coil is formed by repeated windings of a filament to form a structure of continuous turns, resembling a spring. While use of these coils has had some success, questions remain concerning their long-term effectiveness, ease of use, as well as their potential for post procedure migration of embolic material. Post procedure migration is especially of concern when a treatment site is within a peripheral vessel, which may typically be of larger diameter, and have greater blood flow pressure than the vessels of the coronary or cerebral vasculature.

Other attempts have been made to introduce embolic coils having varied stiffness along the length of the coil, with the objective of achieving more secure anchoring in the vessel. However, most of these attempts are directed to the exterior windings of the wires that form the coil. Drawbacks of these techniques include kinking of the coil during the procedure, sometimes resulting in permanent plastic deformation of the coil Kinking and deformation may interfere with accurate placement of the coil, deployment of the coil, and retraction of the coil back into the delivery catheter. Therefore, there remains a need for reliable, kink free deployment and smooth retraction of vessel occlusion coils. Further, there remains a need in the art for a coil having both sufficient flexibility for vessel safety and sufficient stiffness for vessel occlusion and anchoring of the coil within the vessel.

BRIEF DESCRIPTION OF THE DRAWINGS

FIG. 6 illustrates a side view of the embodiment of FIG. 5, deployed within a vessel of a subject.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be routine undertaking for those of ordinary skill in the art having the benefit of this disclosure. The occlusion system disclosed herein boasts a variety of inventive features and components that warrant patent protection, both individually and in combination.

Figure 1:
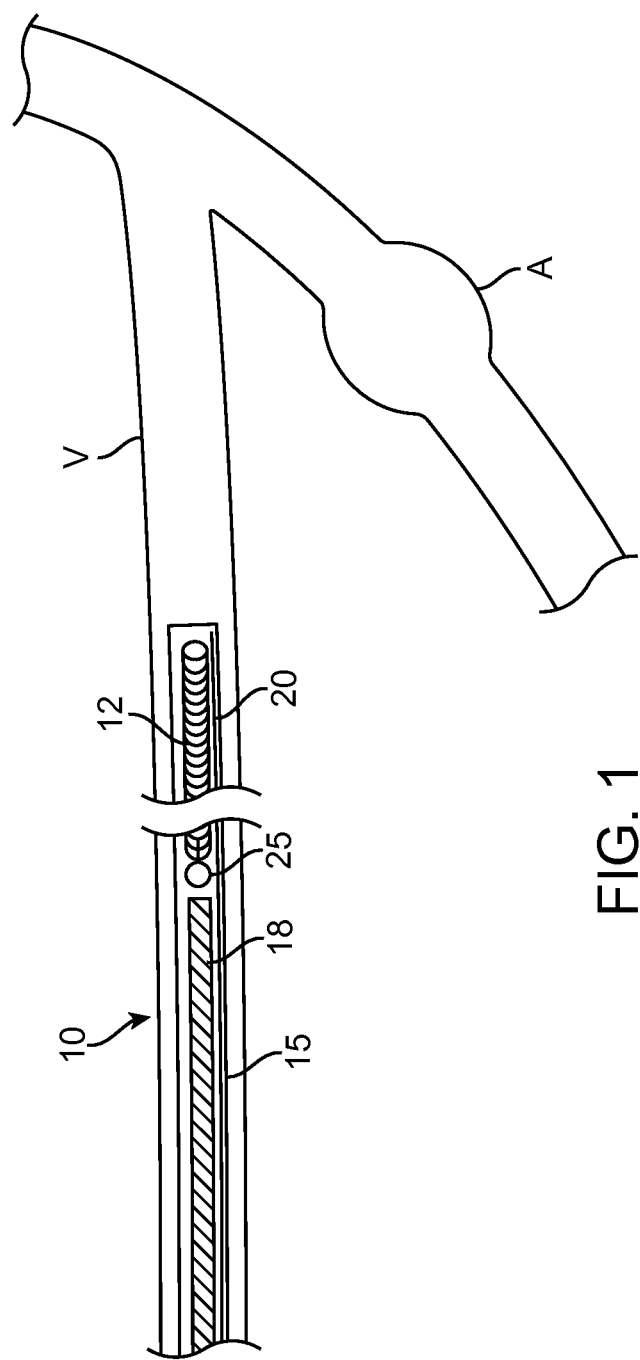
FIG. 1 is a side view of the distal end of a system according to the invention, disposed within a vessel of a subject.

In FIG. 1, a system 10 according to the invention is shown disposed within a vessel V of a subject. Vessel V is a branch of or a feeder vessel to a vessel having an aneurysm A. System 10 includes coil 12. Though alternate delivery techniques and devices are within the scope of the invention, system 10 also includes delivery catheter 15, pusher 18, and pull wire 20. Delivery catheter 15 is an elongate tubular catheter. Pusher 18, coil 12 and pull wire 20 are disposed within delivery catheter 15. Delivery catheter 15 is preferably formed of a polymeric material such as Pebax nylon, urethane, PTFE, Polyimide, metals such as Stainless Steel, Platinum, etc., or other suitable material.

Pull wire 20 extends the length of delivery catheter 15 from its distal end, through its interior, and to its proximal end, where it can be manipulated by a medical practitioner who is performing the procedure to delivery coil 12. Prior to the procedure, coil 12 is chilled to or below its shape transition temperature and loaded into the distal end of delivery catheter 15. While disposed within delivery catheter 15, coil 12 is in an elongate configuration known as its primary configuration. Delivery catheter 15 constrains coil 12 in this primary configuration. Delivery catheter 15 is introduced into the vasculature via an incision, and then tracked to the site where occlusion is desired. Once the treatment site within the vasculature is reached, pusher 18 will be advanced distally within delivery catheter 15 in order to advance coil 12 to the distal tip of delivery catheter 15. Pull wire 20 then acts in conjunction with proximal retention element 25, and the wall of delivery catheter 15, to retain coil 12 in the distal end of delivery catheter 15 until the precise moment that deployment of coil 12 is desired.

Figure 2:
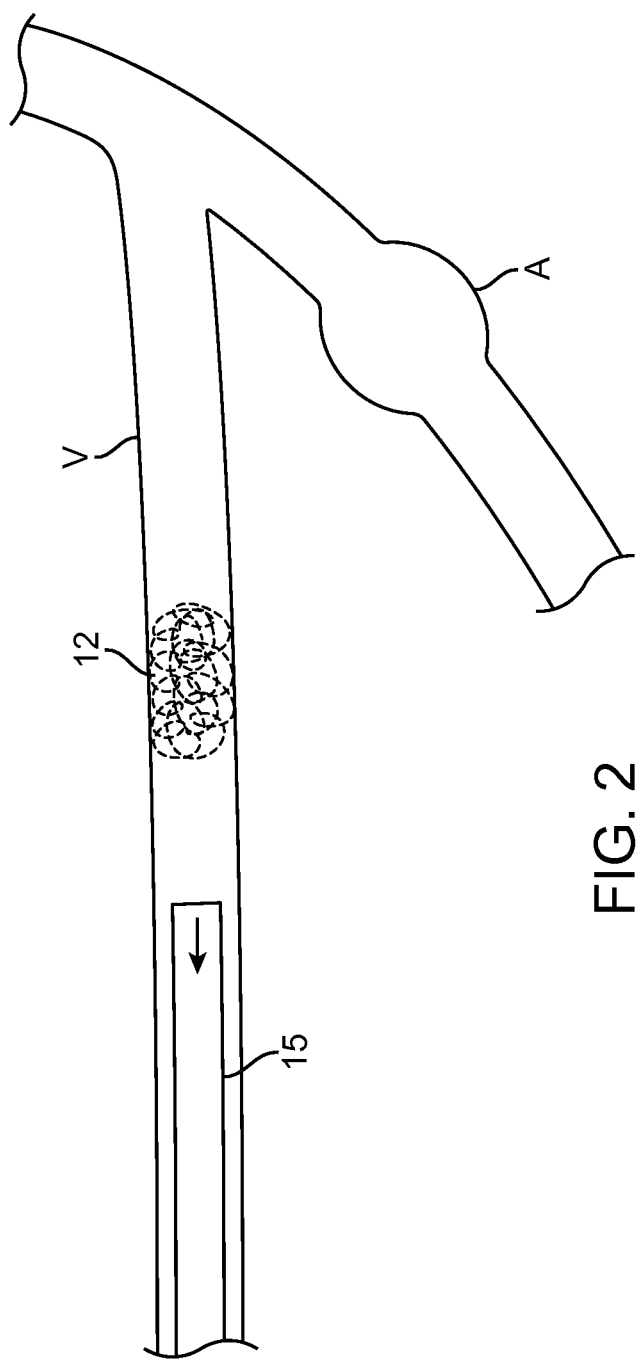
FIG. 2 is a side view of a device according to the invention after the device has been deployed within the vessel.

Following release of coil 12 from delivery catheter 15, coil 12 will transition from its primary, generally linear configuration, to its secondary configuration, as pictured in FIG. 2. In its secondary configuration, coil 12 forms a tightly wound structure that anchors in vessel V. Delivery catheter 15 (and consequently pusher 18 and pull wire 20, not visible in FIG. 2), can then be withdrawn proximally from vessel V. Coil 12 remains implanted within vessel V and prevents blood flow through vessel V, thereby preventing blood flow to a branch vessel having an aneurysm A. As a consequence, vessel V is occluded and sacrificed in order to achieve a therapeutic objective.

Figure 3:
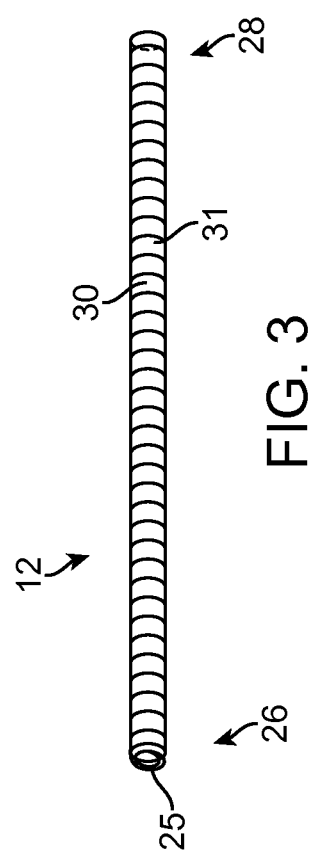
FIG. 3 illustrates a side view of a device according to the invention, where the device is in its primary configuration.

FIG. 3 is a side view of an occlusion coil according to the invention. Coil 12 is shown in its primary configuration, also referred to as its delivery configuration. Coil 12 is illustrated outside of a delivery catheter, yet in its primary configuration so that its features can be more easily viewed. Coil 12 can be described while viewing FIG. 3 from left to right, with its proximal end 26 on the left side of the figure and its distal end 28 on the right. Proximal retention element 25 is visible at proximal end 26. In addition, outer coil 30, and its numerous windings 31 are also visible. Outer coil 30 extends the length of coil 12, from its proximal end 26 to its distal end 28. Outer coil 30 may be constructed from any number of compositions having suitable biocompatibility and performance characteristics. Suitable materials include superelastic Nitinol, platinum, stainless steel, or polymers, including shape memory polymers. Further, materials such as Tungsten, Iridium, and others may be added to confer radio opacity. In the example of coil 12, outer coil 30 is constructed of a Platinum/Tungsten wire of between 0.0015-0.0025 inches thick.

Figure 4:
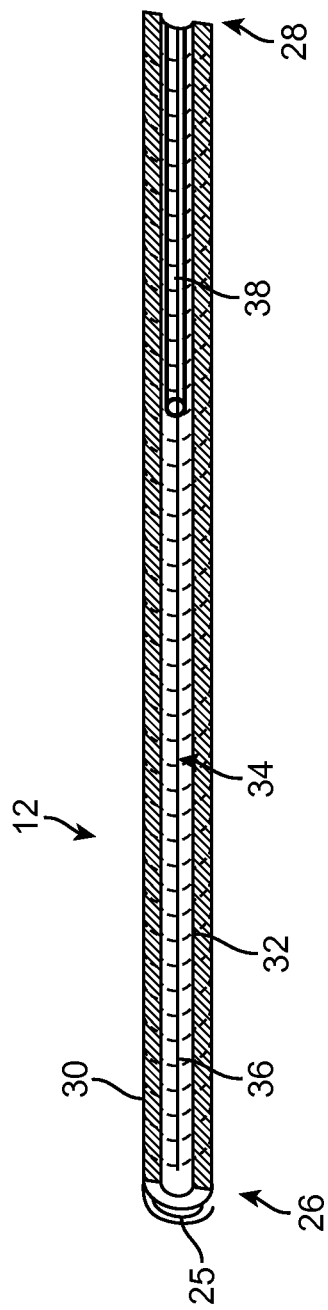
FIG. 4 illustrates a cutaway side view of a device according to the invention, where the device is in its primary configuration.

In order to view the remaining features of coil 12, it is necessary to take a cut-away view of the device. FIG. 4 is a cut-away side view of coil 12. It will be understood that coil 12 is a quite lengthy device that is not drawn to scale in FIG. 4, in order that the features of coil 12 can be more easily viewed. As mention above, outer coil 30 extends the length of coil 12. Disposed within outer coil 30 is optional inner coil 32, which also extends the length of coil 12. Outer coil 30 and inner coil 32 are of similar structure, and may be constructed of either similar or dissimilar materials. Inner coil 32 may be constructed of any of the materials listed above in the description of inner coil 30. Inner coil 32 prevents lateral displacement of successive windings 31 (which are more easily viewed in FIG. 3) and plastic deformation of outer coil 30 during the delivery process, and insures that coil 12 can be retracted into a delivery catheter even after deployment of coil 12.

Disposed within inner coil 32 and visible in the cut away view of FIG. 4 is stretch resistant member 34. Stretch resistant member 34 extends the length of coil 12, but in alternative embodiments, it may be shorter than coil 12. Stretch resistant member 34 terminates in proximal retention element 25 at proximal end 26, and terminates at the opposite end, or distal end 28. A stretch resistant member according to the invention may be constructed from any number of compositions having suitable biocompatibility and shape memory characteristics. Suitable materials include superelastic Nitinol, platinum, stainless steel, or polymers, including shape memory polymers, and any combination of the foregoing. The materials used in the construction of a stretch resistant member according to the invention are generally fabricated into an elongate member such as a wire, filament, braid, cable, or any comparable elongate structure. The terms wire and filament are used interchangeably herein.

A stretch resistant member according to the invention serves two purposes. Firstly, it prevents stretching and/or permanent plastic deformation of coil 12 upon retraction of coil 12. Secondly, it may confer the secondary configuration, or deployment configuration upon coil 12. Alternatively, or in addition, outer coil 30 and/or inner coil 32 may confer a secondary shape on coil 12. In the example of FIG. 4, stretch resistant member 34 is constructed of two components, which will be described in greater detail below. Before assembly of coil 12, a secondary configuration is conferred upon stretch resistant member 34. Due to the shape memory properties of the materials from which stretch resistant member 34 is constructed, stretch resistant member 34 will revert to this secondary configuration when it is not constrained by a catheter, sheath, packaging, or other constraint. Consequently, upon delivery of coil 12 within the subject's vasculature, stretch resistant member 34 returns to this secondary configuration. Because stretch resistant member 34 is disposed within the central lumen of coil 12, it imparts its shape to coil 12. Stretch resistant member is therefore responsible for reconfiguring coil 12 from its primary, or delivery configuration, to its deployment configuration, which is necessary for the effectiveness of the occlusive coil 12.

Stretch resistant member 34 is formed from two components, first member 36 and second member 38. In alternative embodiments according to the invention, a stretch resistant member may be constructed of a single member that is tapered to define a larger diameter end and a smaller diameter end. In the example of FIG. 4, first member 36 extends the length of stretch resistant member 34, is constructed from 0.00125 inch Nitinol wire. First member 36 may be constructed from Nitinol wire that is between 0.00125-0.0025 inches. Second member 38 is coupled to an end of first member 36. Though variations in length are within the scope of the invention, second member 38 extends approximately one third of the length of stretch resistant member 34. Second member 38 is constructed of Nitinol wire of 0.0015-0.0030 inch, but according to the invention may be constructed of any of the materials listed above in relation to the description of stretch resistant member 34, either alone or in combination. In the example of FIG. 4, second member 38 is constructed of a suitable polymer such as polyethylene terephthalate (PET), and is of double width. In an alternative embodiment according to the invention, a single width of a second member may be coupled to a first member.

Second member 38, because it is coupled to first member 36, essentially increases the thickness of stretch resistant member 34 along the length of second member 38. By increasing the thickness of stretch resistant member 34, second member 38 thereby stiffens stretch resistant member 34 along the length of second member 38. Consequently, stretch resistant member 34 has a relatively stiffer coil loop along the length of second member 38, and a relatively soft coil along the length of the segment which is defined solely by first member 36. The stiffer loop exerts greater outward radial force on the vessel wall.

Second member 38 is disposed at the distal end of first member 36. (For other purposes, such as, for example, a reverse anchor for a retrograde deployment, a second member may be coupled to the proximal end of a first member.) Therefore, coil 12 is more stiffly coiled at its distal end 28. This stiffer distal coil exerts greater outward radial force within the vessel, and serves to anchor coil 12 more effectively within the vessel. The softer proximal segment serves to fill the distal anchoring segment defined by second member 38, and coil 12 effectively occludes the subject vessel.

Figure 5:
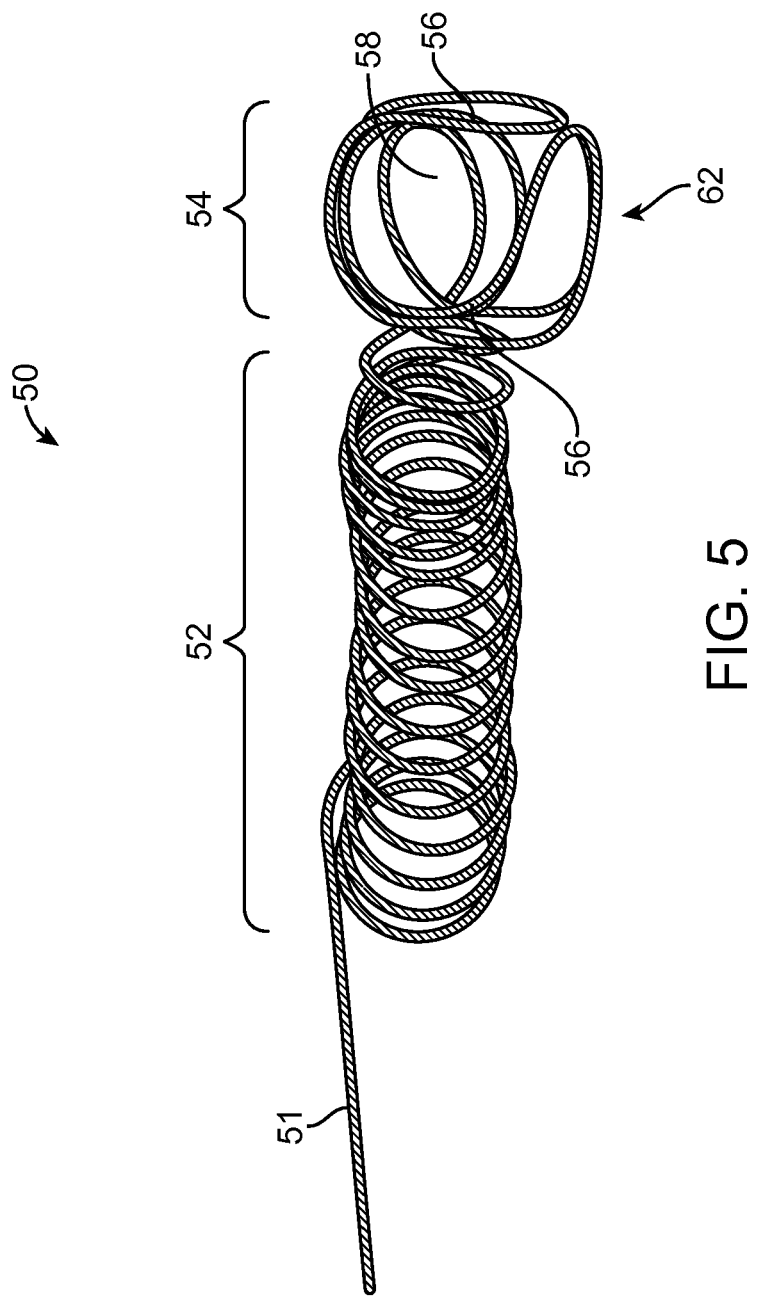
FIG. 5 illustrates a plan view of an alternative embodiment according to the invention, in its deployed configuration, outside of a vessel of a subject.

Turning now to FIG. 5, an alternative embodiment of the invention will be described. FIG. 5 illustrates a plan, or topside view of coil 50 in its deployed configuration, outside a vessel of a subject. Similar to the embodiments described above, the embodiment illustrated in FIG. 5 also has a delivery configuration (not pictured) that is generally linear, that permits the device to be loaded into and delivered via a catheter or comparable delivery tool. Also similar to the embodiments described above, and featured most specifically in FIG. 4, coil 50 includes a stretch resistant member (not visible in FIG. 5) that is disposed within the lumen formed by the helical turns 51 of coil 50, and which confers the secondary or deployed shape upon coil 50. The secondary configuration shown in FIG. 5 may be observed, for example, if the device is deployed on a table top. Vessel occlusion coil 50 has a proximal segment 52. Proximal segment 52 is shaped by a relatively soft or flexible wire or filamentous stretch resistant member (not visible in FIG. 5). The stretch resistant member shaping proximal segment 52 is soft or flexible either because of a small diameter, a fine grind, or other processing step which produces a relatively soft filament. A wide range of flexibility, or softness, of the filament is within the scope of the invention, and the term "relatively" is used here to mean relative to distal segment 54, which will be discussed below.

Proximal segment 52 has a secondary (or deployed) configuration, outside of a vessel that is helical. Alternatively, a proximal segment may have a secondary configuration that is complex, similar to the secondary configuration of distal segment 54, described in more detail below. In yet another alternative embodiment, a proximal segment according to the invention may have a straight or linear configuration. Though a wide range of outer diameters of the helix of proximal segment 52 are within the scope of the invention, in the example illustrated here, the outer diameter of proximal segment 52 is approximately 2-30 mm. In a preferable embodiment, the outer diameter of proximal segment 52 is less than the outer diameter of distal segment 54, when both proximal segment 52 and distal segment 54 are in their secondary configurations. Techniques for forming the secondary configuration of proximal segment 52 are known in the art, and include, for example, wrapping the stretch resistant member disposed within proximal segment 52 around a mandrel and heat treating the segment so that it will return via shape memory behavior to the helical shape. Alternative techniques for achieving the objective are within the scope of the invention.

Vessel occlusion coil 50 also has a distal segment 54, as mentioned above. Distal segment 54 also includes, disposed within its interior and therefore not visible in FIG. 5, a stretch resistant member that is fabricated from a wire, filament, or comparable structure that is stiffer relative to that used to fabricate proximal segment 52. For example, the stretch resistant member of distal segment 54 may be formed from a wire or filament that is of greater thickness than that used to fabricate proximal segment 52. As another example, distal segment 54 may include, similar to that pictured in FIG. 4 above, a second wire member coupled to a first wire member, the second wire member extending only the length of distal segment 54. As yet another example, additional processing steps such as annealing or other steps may be undertaken with respect to the material used to fabricate the filament that forms the stretch resistant member of distal segment 54. Regardless of the technique used to manufacture the stiffer stretch resistant member of distal segment 54, the resulting secondary structure is a stiffer three dimensional object than that of proximal segment 52.

In addition, as can be viewed in FIG. 5, distal segment 54 has a secondary configuration that is more complex than the generally helical shape of proximal segment 52. In an alternative embodiment according to the invention, a distal segment may have a secondary configuration that is helical, similar to the secondary configuration described in more detail above, in relation to the description of proximal segment 52. In the example illustrated in FIG. 5, the deployed shape of distal segment 54 is characterized as having sides 56, top 58, and bottom 62. Taken together, sides 56, top 58, and bottom 62 generally define a cubic shape having rounded corners. Therefore, distal segment 54 can be described as having the shape of a cube. The term "cube" is used here to denote a three dimensional shape having several faces, and a particular embodiment according to the invention may or may not have six faces. The corners and edges of each face may be squared or rounded, curved or straight. Each face may or may not be of equal dimensions as each other face. Further, as is visible in FIG. 5, the secondary shape of distal segment 54 includes some open "interior" space, and much of the coiled element defines the outer edges of the secondary shape of distal segment 54.

In addition to having a very different secondary shape than proximal segment 52, distal segment 54 also has a larger outside profile or outer diameter than proximal segment 52. For example, in the embodiment illustrated in FIG. 5, distal segment 54 has an outer diameter of approximately 3-32 mm. Techniques for shaping distal segment 54 include a series of steps of wrapping the stretch resistant member of distal segment 54 around a specialized mandrel or comparable tool, and heat treating the stretch resistant member so that it returns to the secondary shape imparted by the tool. Alternative techniques for fabricating the stretch resistant member disposed within distal segment 54 are within the scope of the invention.

The combination of both this larger outer diameter, the concentration of material at the outer edges of the shape, and the stiffer internal wire of distal segment 54 cause distal segment 54 to function much like an "anchor" for coil 50 within a vessel. In other words, distal segment 54 exerts some outward radial force against a vessel wall when coil 50 is deployed within a vessel. FIG. 6 illustrates the embodiment of FIG. 5 deployed within a vessel V' of a subject in a manner similar to that described above in relation to alternative embodiments. Distal segment 54 has anchored coil 50 within the vessel. The arrows of FIG. 6 denote the direction of blood flow in the vessel V'. Blood flow in vessel V' causes the softer, smaller diameter proximal segment 52 to flow into and to fill the empty spaces within the deployed distal segment 54. Consequently, proximal segment 52 is essentially within the interior of distal segment 54, and is not as visible as in the illustration of FIG. 5. The resulting structure of vessel occlusion coil 50 is well anchored within vessel V' and is quite dense, and consequently very effective as a vessel occlusion device.

The combinations of stiffer wire and softer wire, smaller diameter and larger diameter, and helical structure and complex structure can be alternated or recombined in a number of combinations if it is desired for the purposes for which the vessel occlusion coil is to be used, and still be within the scope of the invention. For example, an alternative embodiment may have a distal segment that is of helical shape, and the proximal segment could be of a complex shape. Additional alternative combinations are within the scope of the invention if they are desired to achieve a particular clinical objective. In addition, actual outer diameters of both a distal segment and a proximal segment may be desired depending upon vessel size, and result in a coil that is within the scope of the invention.

Among the advantages of the invention herein are its superior anchoring and its kink-resistant, reversible trackability and reversible deployability within tortuous vasculature. It should be recognized that a number of variations of the above-identified embodiments will be obvious to one of ordinary skill in the art in view of the foregoing description. Accordingly, the invention is not to be limited to those specific embodiments and methods of the present invention illustrated and described herein. Rather, the scope of the invention is to be defined by the claims and their equivalents.

What is claimed is:

1. A vessel occlusion coil comprising:
   a first coil having a central lumen;
   an elongate member having a length, the elongate member disposed within the central lumen, said elongate member comprising shape memory characteristics and including a first filament having a length equal to the length of the elongate member and a second filament having a length shorter than the length of the elongate member,
   wherein the second filament is disposed at a distal end of the first filament and is entirely coextensive therewith;
   a retention element configured for releasable retainment disposed at a proximal end of the first coil; and
   wherein the elongate member is relatively stiffer along the length of the second filament and the elongate member is relatively softer along a length where the first filament is present without the second filament.

2. The vessel occlusion coil according to claim 1, wherein said first filament is coupled to said second filament.

3. The vessel occlusion coil according to claim 1, wherein said vessel occlusion coil comprises a proximal end and a distal end, and said second filament is disposed near the distal end.

4. The vessel occlusion coil according to claim 1, wherein said first filament comprises Nitinol and said second filament comprises a polymer.

5. The vessel occlusion coil according to claim 4, wherein said second filament comprises PET.

6. The vessel occlusion coil according to claim 1, wherein said first coil comprises Platinum.

7. The vessel occlusion coil according to claim 1 further comprising a second coil disposed within the central lumen of the first coil.

8. The vessel occlusion coil according to claim 7 wherein said second coil comprises a central lumen and the elongate member is disposed within said central lumen.

9. The vessel occlusion coil according to claim 1 wherein said portion of the length of the first filament is one third of the length of the first filament.

\* \* \* \* \*